(12) United States Patent
Kostovic

(10) Patent No.: US 8,512,962 B2
(45) Date of Patent: Aug. 20, 2013

(54) KIT AND METHOD FOR DETECTING BOVINE VIRAL DIARRHEA VIRUS IN TISSUE SAMPLES

(75) Inventor: Miladin Kostovic, Brookfield, WI (US)

(73) Assignee: Prionics AG, Schlieren (CH)

( * ) Notice: Subject to any disclaimer, the term of this patent is extended or adjusted under 35 U.S.C. 154(b) by 342 days.

(21) Appl. No.: 12/745,877

(22) PCT Filed: Dec. 3, 2008

(86) PCT No.: PCT/US2008/085343
§ 371 (c)(1),
(2), (4) Date: Jun. 2, 2010

(87) PCT Pub. No.: WO2009/073689
PCT Pub. Date: Jun. 11, 2009

(65) Prior Publication Data
US 2010/0240026 A1    Sep. 23, 2010

Related U.S. Application Data

(60) Provisional application No. 60/992,272, filed on Dec. 4, 2007.

(51) Int. Cl.
*G01N 33/53* (2006.01)
*A61K 38/46* (2006.01)
*A61K 39/42* (2006.01)
*A61K 39/00* (2006.01)
*A61K 39/12* (2006.01)

(52) U.S. Cl.
USPC ............................................. 435/7.1

(58) Field of Classification Search
None
See application file for complete search history.

(56) References Cited

U.S. PATENT DOCUMENTS

| | | |
|---|---|---|
| 6,197,755 B1 | 3/2001 | Carrano et al. |
| 6,455,264 B1 | 9/2002 | Baumeister et al. |
| 2002/0142449 A1 | 10/2002 | Kwong et al. |
| 2003/0143573 A1 | 7/2003 | Huchzermeier et al. |

OTHER PUBLICATIONS

Sigma-Aldrich publication, BioFiles for Life Science Research: Enzymes for Cell Dissociation and Lysis, 2006, Issue No. 2.*
Ditcham et al., An immunosensor with potential for the detection of viral antigens in body fluids, based on surface second harmonic generation, 2001, Biosensors and Bioelectronics, vol. 16, pp. 221-224.*
Asenjo and Andrews, Enzymatic Cell Lysis for Product Release, 1990, Bioprocess Technology, vol. 9, pp. 143-175.*
SIGMA, BioFiles: Enzymes for Cell Dissociation and Lysis, 2006, SIGMA-ALDRICH, Issue #2.*

* cited by examiner

*Primary Examiner* — Benjamin P Blumel
(74) *Attorney, Agent, or Firm* — Rankin, Hill & Clark LLP

(57) ABSTRACT

The present invention relates to the method for treatment of tissue samples with proteolytic/histolytic additive collagenase or other similar protease prior to testing with an antigen capture immunoassay to identify cattle infected with Bovine Viral Diarrhea Virus (BVDV). The use of collagenase or other similar protease in antigen extraction step of the assay drastically increases accuracy of the assay, thus it allows for a more effective, reliable, quick, and cost effective way of identifying and thereby removing infected cattle and/or other animals from an otherwise uninfected herd.

14 Claims, No Drawings

KIT AND METHOD FOR DETECTING BOVINE VIRAL DIARRHEA VIRUS IN TISSUE SAMPLES

RELATED APPLICATIONS

The present application claims priority to U.S. provisional application Ser. No. 60/992,272, filed Dec. 4, 2007.

BACKGROUND OF THE INVENTION

Bovine viral diarrhea (BVD) is one of the main multi syndrome diseases affecting cattle that results in a significant economic impact to the cattle industry. Outbreaks of BVD are frequent and global. Economic loss in beef production in affected farms can be in the range of $31-$60 per animal depending on the type of animal production. Many countries in the European Union and businesses in the United States have adopted control programs which are mainly based on vaccination and testing/removing carrier animals.

Common manifestations of BVD include: abortions, infertility, irregular heat cycles, early embryonic deaths, fetal mummification, immunosuppression, diarrhea, fever, pneumonia, and other potentially fatal conditions. BVD cannot be clinically distinguished from other diseases which are manifested with similar symptoms. Immunosuppression lowers the resistance of infected animals to other common pathogens which leads to numerous indirectly caused clinical manifestations in cattle, most commonly bovine respiratory syndrome (BRS). Direct and mostly indirect clinical effect on cattle herds lead to significant economic loss. In rare cases animals can be acutely infected with severe manifestations of the disease. Also animals can be persistently infected when they serve as the reservoir of the infection for other animals.

An animal becomes persistently infected (PI) with Bovine Viral Diarrhea Virus (BVDV) if the fetus is exposed to slow-growing, low-virulence strains of the virus between days 30 and 125 of gestation. Fetuses exposed to BVDV after 125 days of gestation will mount an immune response against the virus, which clears the infection and usually develop quite normally. Fetuses exposed to a rapidly growing or "HOT" strain of the virus are usually killed. PI animals lack immunity to BVDV and are lifetime carriers of the virus. PI animals shed several billion viral particles a day and serve as a reservoir of BVDV in a herd. Animals that are exposed to BVDV acutely may become infected and shed a virus for a few days until they present an immune response. These animals recover from the infection and do not remain carriers.

Strategies for control of BVDV include vaccination, management practices, and most importantly strict biosafety measures. Vaccination is not very effective due to the high variability of the virus which causes BVD. Biosafety measures involve testing of all animals which are introduced to the herd and separation of all PI animals so that they cannot cause infection in naive cattle (non-infected). Non-specific symptoms and failure of field vaccinations for BVDV increase the need for a test protocol that will help identify and eliminate carrier PI animals in a cost-effective manner.

BVD is caused by BVDV. BVDV is an umbrella term for a diverse group of viruses in the genus pestivirus of the family Flaviviridae. It is further classified into two different genotypes known as BVDV1 and BVDV2, which represent two distinct species. Within each genotype there are many different strains of the virus that differ significantly in their pathogenesis. Severe acute disease has only been reported with small number of BVDV2 strains. In addition, BVDV is classified into three different biotypes based on their cytopathic effect when grown in vitro: cytopathic which degenerate epithelial cells in vitro, non-cytopathic which does not degenerate epithelial cells in vitro and lymphocytopathic which degenerates lymphocytes in vitro, but it does not degenerate epithelial cells (Ridpath et al., Lymphocytopathogenic activity in vitro correlates with high virulence in vivo for BVDV type 2 strains: Criteria for a third biotype of BVDV. Virus Res. 2006). Lymphocytopathic biotype correlates with high virulence in acute infections. Due to the aforementioned factors BVDV is not to be limited to a specific strain of virus, but rather refers to an umbrella of pathogenic and benign organisms within the genus Pestivirus.

Organisms in the genus Pestiviruses have a positive sense single stranded RNA genome (SS+RNA). Organisms referred to as BVDV contain a genome of approximately 12,500 nucleotides with a 5'-nontranslated region (NTR), a single large open reading frame (ORF), and a 3'-NTR lacking a poly(A)tail. The 5'-NTR contains an internal ribosome entry site that initiates translation of BVDV mRNA. The secondary structure of the 5'-NTR is involved in the regulation of translation and genome replication. The genomic RNA has one open reading frame (ORF) of about 4000 codons whose translation yields one precursor poly protein, which is co- and post translationally cleaved into 11 or 12 mature proteins, by viral and host cell encoded proteases ("processing"). Most of the virally encoded cleaving is catalyzed by a serine protease domain within the non-structural protein NS3 and generates the non-structural proteins NS3 to NS5B, whereas the structural proteins are believed to be cleaved by cellular proteases.

BVDV virions consist of four structural proteins (Meyers et al., Molecular characterization of pestiviruses. Adv Virus Res. 1996); nucleocapsid C protein, envelope glycoproteins Erns, E1 and E2. Along with the structural proteins described above, the viral genome encodes several non-structural proteins (Npro, p7, NS2/3, (NS2, NS3), NS4A, NS4B, NS5A and NS5B) which are essential for replication of the virus. BVDV proteins and their function are described in TABLE 1.

TABLE 1

| | |
|---|---|
| C | Capsid protein (core protein). |
| Erns | Envelope glycoprotein (rns means Rnase secreted); induces production of antibodies with a weak neutralizing activity. |
| E1 | Envelope glycoprotein. |
| E2 | Envelope glycoprotein; it features epitopes that are recognized by the host immune system. Antibodies against these epitopes are essential for the neutralization of viral infectivity. |
| p7 | Very small protein with largely unknown function. Essential for the formation of infective virus particles. |
| Npro | The N-terminal protein of BVDV codes for a cysteine protease that cleaves the N-terminus from the core protein (auto-protease). |
| NS2/3 | Serine protease; biggest BVDV-protein with a molecular weight of 125 kD; cytopathic BVDV does not only express NS2/3 in vitro in one piece but also in two separate proteins (NS2, 54 kD and NS3, 80 kD, commonly called p80). In this application and the appended claims, NS2/3 will be used to reference NS2/3, NS2, NS3 or any part of these molecules, unless otherwise stated. |
| NS4A/B | NS4A is a cofactor for serine protease NS2/3; there's evidence that NS4B plays a role in viral cytopathogenicity; both do not induce an immune response. |

TABLE 1-continued

| | |
|---|---|
| NS5A | NS5A is part of the replication complex. |
| NS5B | NS5B is RNA dependent RNA-polymerase. |

Diagnostic tests for BVD are oriented toward detection of the presence of viral antigens or viral RNA in bodily fluids or tissue samples. Positive animals are considered carriers of BVDV and are separated from other animals to prevent disease spread through the herd. One sole PI animal has the ability to infect every animal in direct contact. Given this information it is essential that diagnostic tests have very high sensitivity in order to adequately identify every PI animal.

Current BVDV detection methods include: Polymerase Chain Reaction (PCR), standard viral isolation techniques (i.e. culture), immunohistochemistry, and antigen capture enzyme-linked immunoassay (ELISA). PCR technology amplifies and detects the viral RNA. This makes PCR extremely sensitive, but also this method is prohibitively expensive to the cattle industry. In order to counter the expense the laboratories have decided to batch several individual samples together to create a pooled sample, and then test the pooled sample. The inherent problem with this approach is that if the pool sample is positive for the virus the lab cannot determine which individual samples within the pooled sample contain the virus. In this instance all of the original samples must be retested individually to determine which cattle are affected. Also inhibitory factors can lead to false negative PCR reactions. This problem is amplified by the use of pooled samples. Viral RNA is relatively unstable and false negative reactions can be observed. All those limitations lead to lower sensitivity and questionable usefulness of pooled PCR technique (Edmondson et al., Comparison of tests for detection of bovine viral diarrhea virus in diagnostic samples. J Vet Diagn Invest. 2007). Viral isolation by culture is costly, very complex, time consuming, and can only be performed in a few specialized laboratories limiting its appeal. Immunohistochemistry is also a costly, very complex, and labor intensive technique reserved only for specialized laboratories also limiting its appeal.

ELISA technology however is well suited as a broad based diagnostic tool because it is relatively inexpensive, simple, reproducible and can be performed almost anywhere. Currently ELISA testing for the presence of the viral antigens is done in most cases using ELISA system that detects Erns protein. Erns represents a structural glycoprotein and as such is a part of the envelope of the virus. Thus, it is present in infected cells, as well as outside of infected cells in circulation. Sensitivity of this ELISA system based on the detection of Erns protein is in the range of 99.7% per our experiments on animals three months or older. This technology is patented (U.S. Pat. No. 7,449,288) and is available from one commercial supplier. There are also a minimum of three ELISA tests available, based on the detection of NS2/3 protein. Commercially those tests are not significant because they generally show lower sensitivity then Erns based ELISA (95.5% sensitivity according to our experiments and also according to some external studies (IDEXX Laboratories, internal data). Recently published papers show that NS2/3 protein and its derivative NS3 protein are not suitable for detecting BVDV in cattle because: NS3 molecule is unstable, it is not uniformly distributed in tissues and there is only a small quantity of it to detect (R. A. Fux, Dissertation, University of Munich, 2007). The disclosed methodology presents a much improved method of detecting non-structural proteins such as NS2/3. Disclosed technology overcomes problems of solubility of NS2/3 protein, its stability and drastically increases the quantity of the available antigen for detection with NS2/3 specific antibodies.

SUMMARY OF THE INVENTION

The method and system identified in this disclosure refers to a specific treatment of tissue samples prior to detection of the bovine viral diarrhea virus (BVDV) antigens. This is achieved by a novel extraction buffer which incorporates a proteolytic/histolytic agent such as collagenase derived from *Clostridium histolyticum* or other proteases, allowing for lysis of the infected cells in solution therefore releasing the viral antigens trapped within. Throughout this application and in the appended claims, the term "collagenase" refers to an enzyme or group of enzymes that catalyzes the degradation of collagen. Furthermore, this lytic process has also been found to solubilize NS2/3 protein therefore making it more detectable. In contrast to some proteases (e.g. trypsin or proteinase K, collagenase derived from *Clostridium histolyticum* shows no adverse effects against an NS2/3 protein over time.

The present method for detecting an NS2/3 protein in a sample comprises:
a) subjecting the sample to suitable solution of collagenase or other protease, under which tissue is lysed and structural and non-structural proteins are released and solubilized;
b) incubating a sample extract with a ligand that can preferentially bind to NS2/3 under conditions suitable to afford binding of the ligand; and
c) detecting NS2/3-bound to ligand produced in step b), whereby the amount of bound ligand correlates with the quantity of NS2/3 present in the sample.

This process allows for superior sensitivity when dealing with minute quantities of the BVDV virus, and allows for detection of the virus in samples that were not detectable before this invention.

The novel use of the proteolytic enzymes collagenase, allow for the development of an enhanced assay for BVDV. The immunoassay provided thereby is accurate, has a shorter turnaround time for a given test sample, is more reliable, is more sensitive, and is less expensive.

As will be recognized by persons of skill in the art, and considering similar composition of viral proteins, other types of pestiviruses can be detected using described methodology in detection of viral antigens in tissue samples.

The method and system described herein may be used on domestic and wild animal populations (e.g. deer, moose, elk) to determine if they are BVDV positive in order to aid in the management of domestic and wild animal populations and assist in the removal of reservoirs of BVDV in and outside the domestic cattle population.

Furthermore, the use of a collagenase extraction buffer according to the invention does not interfere with subsequent PCR reactions on the same extract, thus enabling users to run both tests on the same extract.

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structures.

While the preferred embodiment has been described, the details may be changed without departing from the invention, which is defined by the claims.

In one embodiment the method and system described herein may be a sandwich type immunoassay, employing anti-NS2/3 antibodies adhered to a solid substrate as antigen capture antibodies, and another anti-BVD viral antigen antibody as a detection antibody (a labeled antibody that allows the reaction to be detected). The method and system described herein may also be a competitive type immunoassay by again employing anti-NS2/3 antibodies to a solid substrate as antigen capture antibodies, allowing them to react with free NS2/3 in a sample, and then exposing the remaining antibodies to labeled detection antigen NS2/3 and detecting the presence of labeled NS2/3.

Further configurations and formats are possible for each type of immunoassay. The capture antibody, for example, can be attached to a variety of solid substrates such as polystyrene, glass, PVC, nitrocellulose, or other similar compounds.

For a sandwich type assay, primary antibody, also called capture antibody, in this case anti-NS3 antibody, may be attached to a solid phase by passive adsorption, covalent coupling, or by using a solid phase pre-coated with a secondary binder such as avidin or an antibody specific for anti-NS2/3.

For a competitive binding type immunoassay, anti-NS3 antibody may be attached to a solid phase by passive adsorption, covalent coupling, or by using a solid phase pre-coated with a secondary binder such as avidin or an antibody specific for anti-NS3.

For another alternate competitive binding immunoassay the anti-NS3 antibody is to be freely suspended in liquid solution similar to the method described in U.S. Pat. No. 4,868,131. The antibody will either bind with NS2/3 from the sample, or bind with NS2/3 labeled with a large particle. The solution will then be passed through a porous layer allowing the anti-NS2/3 with unlabeled NS2/3 to pass, and the anti-NS2/3 with labeled NS2/3 to remain.

For another alternate competitive binding immunoassay, the Anti-NS2/3 may be used in an HPLC based competitive binding immunoassay.

In still other embodiments, a variety of labels can be employed on detection antibody in sandwich or detection antigen in competitive type immunoassays. The possibilities include: an enzyme such as peroxidase or alkaline phosphatase, a fluorophore such as fluorescein, a chemiluminescent probe such as an acridinium ester, a time resolved fluorescent probe such as europlum chelate, a radioactive species, or particles such as colloidal gold, plain latex, or dyed latex.

The NS2/3 specific detection antibody may be directly labeled by covalent coupling. A labeled secondary antibody that is specific for the corresponding primary antibody may be used without the need to chemically modify the primary antibody. A labeled secondary binder such as avidin, or a labeled antibody specific for a particular ligand (i.e. dinitrophenol, fluorescein, and others) can also be employed. In the case of avidin or any of the ligand specific antibodies, it is necessary to covalently attach the corresponding ligand to the primary antibody.

For a competitive type assay, the NS2/3 antigen can be labeled directly by covalent coupling or a labeled secondary binder, such as avidin or a labeled antibody specific for a particular ligand (i.e. dinitrophenol, fluorescein, and others) can be employed. In this case of avidin or any of the ligand specific antibodies, it is necessary to covalently attach the corresponding ligand to the NS2/3 antigen.

Exemplary Reagents

An extraction buffer for use in the kit and method of the invention comprises collagenase, water and other optional components. The concentration of collagenase is not per se critical. At higher concentrations, a relatively short amount of time is required to obtain the desired extraction. At lower concentrations, the extraction will still be effective, but will take a relatively longer period of time. In view of the foregoing, the preferred concentration of collagenase is from about 1 to about 20 mg/ml, more preferably from about 2 to about 15 mg/ml and most preferably about 5 mg/ml.

The pH of the extraction buffer is also not per se critical. The extraction buffer can have a pH of from about 5.0 to about 9.0, with a pH of from about 6.5 to about 8.0, or about 7.4 being preferred.

The extraction buffer is to be made prior to use and should be kept refrigerated at 2-8 degrees C. until use, preferably for a maximum of five days prior to use. The extraction buffer can further comprise other optional components, provided the optional components do not adversely affect the extraction buffer.

An exemplary ELISA extraction buffer according to the invention comprises 0.1% Igepal and approximately 5 mg/ml of collagenase in phosphate buffered saline (PBS) at pH 7.4. Also 0.1% v/v ProClin 300 is added to prevent contamination and 4 mg/ml of Phenol Red is added for coloring and pH check. As noted above, the concentration of collagenase used varies between lots of produced compound.

An exemplary ELISA wash buffer comprises 0.05% Tween 20 in PBS at pH 7.4. Other ELISA wash buffers known in the art can be used.

An exemplary diluent buffer comprises 0.1% Bovine Serum, 0.1% ProClin 300, and 0.5% Tween 20 in PBS (pH 7.4). Other diluent buffers known in the art can be used.

In one embodiment a commercially available tetramethylbenzidine (TMB) substrate is used. Suppliers of this substrate include: Pierce Chemical Co., Kirkegaard & Perry Laboratories, SurModics Corporation and others. Depending on the label of the ligand, other substrates could be used.

Further exemplary compounds include a "stop solution" which consists of 1% hydrochloric acid (HCl). Other stop solutions known in the art can be used.

A coating solution is used to coat the solid support, like plastic wells of microtiter plate. An exemplary coating solution comprises 0.1 ml of purified primary antibody (anti-NS2/3) in a carbonate buffer at a pH 9.6. The approximate concentration of the antibody is 1 mg/L.

A conjugate reagent must also be used in order to provide for detection. An exemplary conjugate reagent comprises horseradish peroxidase conjugated anti-NS2/3 MoAb at a concentration approximate to 1 mg/L, 0.1% ProClin 300, and 50% StabilZyme (SurModics Corporation) in PBS at pH 7.4. The composition of the conjugate reagent can be modified, as necessary.

In a preferred embodiment, the negative control for the assay kit comprises 1% bovine serum and 0.1% ProClin 300 in PBS pH 7.4.

And, in a preferred embodiment, the "positive control" for the assay kit comprises 1% bovine serum, ProClin 300 and purified BVDV antigen of a final concentration capable of providing a reaction value of 1.000 OD.

The "sample extract" preferably comprises at least 20 micrograms of skin tissue in 200 microliters of extraction buffer incubated overnight at room temperature (20-25 degrees C.) in extraction tubes (test tubes provided in the kit).

Exemplary Embodiments

In one exemplary embodiment directed toward anti-BVDV antibody-coated wells a 96 well micro titer plate is used. Each individual well is coated overnight with "coating antibody" solution and incubated overnight at 2-8° C. Following the incubation each tray is washed four times with ELISA wash buffer solution, after which each well is filled with 1% solution of bovine serum albumin in PBS pH 7.4. After one hour incubation at room temperature plate is washed four times with ELISA wash buffer and then allowed to dry overnight at room temperature at <30% humidity. A foil pouch is used to encase each tray after drying, and a desiccant is included within the pouch to remove moisture.

In one embodiment, in order to efficiently run the test a coated microtiter plate is to be removed from its foil pouch. The user is to remove an adequate number of wells for their test volume from the microtiter plate and return any excess wells to the foil pouch for future use. The user is to transfer 0.1 ml of sample extract post incubation into the microtiter well designated for that sample. Multiple samples may be run simultaneously as long as each sample is transferred to a separate well, and none of the samples become contaminated in the process.

In one embodiment, after the addition of the sample extract, user then covers the inoculated wells with a self-adhesive transparent film, and incubate the wells for one hour at room temperature (20-25° C.) or overnight at refrigerator temperature (4-8° C.).

After this incubation period, the user removes the liquid remaining in the microtiter wells and washes the wells by adding 0.2-0.35 ml of ELISA Wash buffer to each well, and then manually removing or pouring off the ELISA Wash Buffer. This wash process is to be repeated three additional times to yield a total of four washes.

In one embodiment, after the washing of all wells, user then adds 0.1 ml of diluted labeled detection antibody (conjugate) to all wells, and incubate the wells for one hour at room temperature (20-25° C.).

After this incubation period, the user removes the liquid remaining in the microtiter wells and washes the wells by adding 0.2-0.35 ml of ELISA Wash buffer to each well, and them manually removing or pouring off the ELISA Wash Buffer. This wash process is to be repeated three additional times to yield a total of four washes.

After washing, 0.1 milliliters of TMB should be pipetted into each microtiter well. The wells are to be covered with adhesive film and incubated for 15 minutes at room temperature (20-25° C.), After this incubation period 0.1 milliliters of stop solution are to be pipetted into each microtiter well. Once stop Solution is added, the sample is ready to be read at 450 nm on a microplate reader, or other suitable spectrophotometer.

Positive samples will produce color, while negative samples will cause no color production.

With regard to the above protocol, it should be noted that to insure the accuracy and quality of results obtained, both positive and negative controls should be included in each run. The BVDV Antigen Test Kit itself should be stored at 2-8° C. in order to maintain its shelf life and effectiveness for as long as possible.

Due to the fact that an acute BVDV infection can result in the production of BVDV antigens over a short period of time, a BVDV-positive result in the immunoassay may not always be indicative of a persistently infected animal. A definitive diagnosis that a particular animal is persistently infected should only be made after a second sample is taken from the subject animal at least 3 weeks after the initial sample and that second sample is also found to be BVDV-positive.

Example

Table 2 shows exemplary data from paired test runs of samples which were not treated with a proteolytic agent, instead just with the standard extraction buffer containing Triton X-100, and results of samples which were treated with an extraction buffer as described in this disclosure using collagenase as the proteolytic agent. All untreated samples show a low optical density value, thus are scored negative in the test, while all samples treated with collagenase extract show a positive result. Table 2 only includes the most difficult samples run while most other samples show drastic increase in signal of more than 400%. All samples used in the study were from confirmed PI positive animals.

TABLE 2

| # | Untreated Samples | | Treated Samples | |
|---|---|---|---|---|
| 1 | 0.078 | 0.065 | 2.510 | 2.526 |
| 2 | 0.084 | 0.106 | 0.236 | 0.234 |
| 3 | 0.084 | 0.080 | 0.566 | 0.567 |
| 4 | 0.104 | 0.130 | 1.068 | 1.071 |
| 5 | 0.091 | 0.077 | 0.305 | 0.287 |
| 6 | 0.084 | 0.090 | 0.408 | 0.423 |
| 7 | 0.088 | 0.090 | 1.306 | 1.269 |
| 8 | 0.168 | 0.152 | 3.112 | 3.143 |

Accordingly it is to be understood that the embodiments of the invention herein described are merely illustrative of the application of the principles of the invention. Reference herein to details of the illustrated embodiments is not intended to limit the scope of the claims, which themselves recite those features regarded as essential to the invention. While the preferred embodiment has been described, the details may be changed without departing from the invention, which is defined by the claims.

What is claimed is:

1. A kit for detecting BVDV antigens in a biological sample, the kit comprising:

a solution comprising collagenase derived from *Clostridium histolyticum* capable of lysing cells in the biological sample to release and solubilize BVDV antigens;

a primary antibody that binds to BVDV antigens; and a labeled antigen that binds to the primary antibody and/or a labeled antibody that binds to BVDV antigens.

2. The kit according to claim 1, wherein the primary antibody binds to non-structural BVDV protein NS2/3.

3. The kit according to claim 1, wherein the concentration of collagenase in the solution is from about 1 to about 20 mg/ml.

4. The kit according to claim 1, wherein the primary antibody is attached to a solid phase support.

5. The kit according to claim 1, wherein the labeled antigen and/or the labeled antibody includes a color-producing label.

6. The kit according to claim 1, wherein the labeled antigen and/or the labeled antibody includes an enzyme.

7. The kit according to claim 1, wherein the labeled antigen and/or the labeled antibody includes a fluorescent label.

8. A method for detecting BVDV antigens in a biological sample, the method comprising:

contacting the biological sample with a solution comprising collagenase derived from *Clostridium histolyticum* capable of lysing cells in the biological sample to release and solubilize BVDV antigens;

contacting the BVDV antigens released from the biological sample with a primary antibody that binds to BVDV antigens, and
- a labeled antibody for detecting the binding of the BVDV antigens to the primary antibody; and detecting the BVDV antigens bound to the primary antibody via the labeled antibody.

9. The method according to claim 8, wherein the primary antibody binds to non-structural BVDV protein NS2/3.

10. The method according to claim 8, wherein the concentration of collagenase in the solution is from about 1 to about 20 mg/ml.

11. The method according to claim 8, wherein the primary antibody is attached to a solid phase support.

12. The method according to claim 8, wherein the labeled antibody includes a color-producing label.

13. The method according to claim 8, wherein the labeled antibody includes an enzyme.

14. The method according to claim 8, wherein the labeled antibody includes a fluorescent label.

* * * * *